(12) United States Patent
Zhou et al.

(10) Patent No.: US 9,511,097 B2
(45) Date of Patent: Dec. 6, 2016

(54) REGENERATION OF CORONARY ARTERY BY CORONARY ENDOTHELIAL SPECIFIC PROGENITOR CELLS

(71) Applicant: Albert Einstein College of Medicine, Inc., Bronx, NY (US)

(72) Inventors: Bin Zhou, Bronx, NY (US); Bingrou Wu, Bronx, NY (US)

(73) Assignee: Albert Einstein College of Medicine, Inc., Bronx, NY (US)

( * ) Notice: Subject to any disclaimer, the term of this patent is extended or adjusted under 35 U.S.C. 154(b) by 0 days.

(21) Appl. No.: 14/443,075

(22) PCT Filed: Nov. 20, 2013

(86) PCT No.: PCT/US2013/070911
§ 371 (c)(1),
(2) Date: May 15, 2015

(87) PCT Pub. No.: WO2014/081772
PCT Pub. Date: May 30, 2014

(65) Prior Publication Data
US 2015/0290250 A1 Oct. 15, 2015

Related U.S. Application Data

(60) Provisional application No. 61/728,610, filed on Nov. 20, 2012.

(51) Int. Cl.
| | |
|---|---|
| *C12N 5/071* | (2010.01) |
| *A61K 35/44* | (2015.01) |
| *A01K 67/027* | (2006.01) |
| *C12N 15/85* | (2006.01) |
| *C07K 16/22* | (2006.01) |

(52) U.S. Cl.
CPC ........... *A61K 35/44* (2013.01); *A01K 67/0275* (2013.01); *C07K 16/22* (2013.01); *C12N 5/069* (2013.01); *C12N 15/8509* (2013.01); *A01K 2217/072* (2013.01); *A01K 2217/206* (2013.01); *A01K 2227/105* (2013.01); *A01K 2267/0375* (2013.01); *A01K 2267/0393* (2013.01); *C07K 2317/76* (2013.01); *C12N 2501/165* (2013.01); *C12N 2506/1315* (2013.01); *C12N 2840/203* (2013.01)

(58) Field of Classification Search
CPC .... A61K 35/44; C12N 5/069; C12N 2501/165
See application file for complete search history.

(56) References Cited

U.S. PATENT DOCUMENTS

2011/0207664 A1    8/2011   Alitalo et al.

OTHER PUBLICATIONS

PCT International Search Report and Written Opinion, dated Apr. 23, 2014 in connection with PCT International Application No. PCT/US2013/70911, 12 pages.
Lee Y M et al., entitled "Vascular Endothelial Growth Factor Receptor Signaling is Required for Cardiac Valve Formation in Zebrafish," Developmental Dynamics, Sep. 16, 2005, vol. 235, pp. 29-37.
Patel-Hett S et al., entitled "Singal transduction in vasculogenesis and developmental angiogenesis," Int J Dev Biol, 2011, vol. 55, No. 4-5, pp. 353-363.
Wu B et al., entitled "Endocardial Cells Form the Coronary Arteries by Angiogenesis through Myocardial-Endocardial VEGF Signaling," Cell, Nov. 21, 2012, vol. 151, No. 5, pp. 1083-1096.

*Primary Examiner* — Daniel C Gamett
(74) *Attorney, Agent, or Firm* — Amster, Rothstein & Ebenstein LLP

(57) ABSTRACT

Methods and products are provided for producing an artery-specific endothelial cell. Also provided are methods for treating a tumor in a subject.

15 Claims, 7 Drawing Sheets

REGENERATION OF CORONARY ARTERY BY CORONARY ENDOTHELIAL SPECIFIC PROGENITOR CELLS

CROSS-REFERENCE TO RELATED APPLICATIONS

This application is a U.S. national stage entry under 35 U.S.C. §371 of PCT International Patent Application No. PCT/US2013/70911, filed on Nov. 20, 2013, which claims the benefit of U.S. Provisional Patent Application No. 61/728,610, filed on Nov. 20, 2012, the contents of all of which are herein incorporated by reference.

STATEMENT OF GOVERNMENT SUPPORT

This invention was made with government support under grant number HL007881 awarded by the National Institutes of Health. The government has certain rights in the invention.

BACKGROUND OF THE INVENTION

Throughout this application various publications are referred to in parentheses. Full citations for these references may be found at the end of the specification. The disclosures of these publications, and all patents, patent application publications and books referred to herein, are hereby incorporated by reference in their entirety into the subject application to more fully describe the art to which the subject invention pertains.

Despite the medical importance of coronary arteries, their embryonic origins and developmental mechanisms remain unclear. These arteries are the loci for coronary artery disease, the most widespread disease in western societies. Elucidating mechanisms of coronary artery formation may help recapitulate this developmental process for coronary artery regeneration.

Coronary arteries have 3 tissue layers: the inner layer of endothelium, the middle layer of smooth muscle cells, and the outer layer of fibroblasts. The endothelium is the first layer formed during coronary artery formation. Primitive coronary vessels (or coronary plexuses) consist of one endothelial cell layer. The plexuses then recruit smooth muscle cells and fibroblasts to assemble mature arteries. Endothelium is also the first site where coronary artery disease occurs in adults. Thus identifying the cellular origins of coronary endothelium is essential to elucidate mechanisms of coronary artery development or regeneration.

The heart is made of three major tissue layers: the endocardium, myocardium, and epicardium. The myocardium is the central layer, and the coronary vasculature forms within this layer during development. The epicardium is the outermost epithelial layer of the heart; it is derived from the proepicardium outside the heart (Komiyama et al., 1987; Viragh and Challice, 1981). Studies have shown that epicardial cells generate coronary vascular smooth muscle cells (Cai et al., 2008; Dettman et al., 1998; Mikawa and Fischman, 1992; Mikawa and Gourdie, 1996; Vrancken Peeters et al., 1999; Zhou et al., 2008). It is less clear whether proepicardial/epicardial cells make any significant contribution to coronary endothelial cells, although some coronary endothelial cells in avian species are derived from proepicardial cells (Mikawa et al., 1992; Perez-Pomares et al., 2002). Fate-mapping studies in mice have suggested the sinus venosus as a common origin of the endothelium of coronary arteries and veins (Red-Horse et al., 2010) while a subset of proepicardial cells also contribute to some coronary endothelial cells (Katz et al., 2012).

The endocardium is the internal epithelial layer of the heart. Endocardial cells are one of the earliest endothelial populations acquired in development, differentiating from multipotent progenitors in the cardiac field (Misfeldt et al., 2009; Sugi and Markwald, 1996; Yamashita et al., 2000; Yang et al., 2008). They form an endocardial tube by vasculogenesis and later become the endocardium of the heart (Drake and Fleming, 2000). Endothelial cells of coronary vessels arise later in development and form coronary vessels in the myocardium (Lavine and Ornitz, 2009; Luttun and Carmeliet, 2003; Majesky, 2004; Olivey and Svensson, 2010; Wada et al., 2003). Ventricular endocardial cells have been thought to be terminally differentiated without a significant role in coronary vessel formation. However, even in light of this knowledge, coronary artery regeneration technology is still in need of better understanding and techniques.

The present invention addresses this need by providing novel coronary artery regeneration methods and compositions.

SUMMARY OF THE INVENTION

Also provided is a method of treating a tumor in a subject comprising administering an inhibitor of Vegf-a or of Vegfr-2 to the subject in a manner permitting the inhibitor of Vegf-a or of Vegfr-2 to enter the tumor, thereby treating the tumor.

Also provided is a method of determining whether an agent specifically promotes the growth of coronary artery-specific endothelial cells comprising contacting an Nfatc1+ endocardial cell, or contacting an inducible pluripotent stem cell in which Nfatc1+ has been induced, with an amount of an activator of Vegfr-2 or of Vegf-a under conditions permitting the cell to produce an artery-specific endothelial cell from the inducible pluripotent stem cell or Nfatc1+ endocardial cell, and measuring the extent of growth of the artery-specific endothelial cell in the presence of, and in the absence of, the agent, wherein an increased growth of artery-specific endothelial cells in the presence of the agent as compared to in the absence of the agent indicates that the agent specifically promotes the growth of coronary artery-specific endothelial cells, and wherein a decreased, or no increase in, growth of artery-specific endothelial cells in the presence of the agent as compared to in the absence of the agent indicates that the agent does not specifically promote the growth of coronary artery-specific endothelial cells.

Also provided is a method of treating a heart condition in a mammalian subject comprising administering to the subject an amount of the artery-specific endothelial cells produced by any of the instant methods or an amount of any of the instant compositions effective to treat the heart condition in a mammalian subject.

A composition is provided comprising a plurality of isolated artery-specific endothelial cells produced by any of the instant methods.

A method is provided for producing an artery-specific endothelial cell comprising contacting an Nfatc1+ endocardial cell, or contacting an inducible pluripotent stem cell in which Nfatc1+ has been induced, with an amount of an agent that activates Vegfr-2 effective to produce an artery-specific endothelial cell from the Nfatc1+ endocardial cell or inducible pluripotent stem cell.

BRIEF DESCRIPTION OF THE DRAWINGS

FIG. 5A-5L. Disruption of Vegf-a in the myocardium reveals that myocardial Vegf-a is required for coronary angiogenesis and artery formation (A-D) Pictures of E12.5 Tnnt2Cre;Vegf-a+/+ (Control) heart stained with Pecam1 antibodies exhibit coronary plexuses (arrows) in the peritruncal region and interventricular septum (ivs). Arrowheads indicate the branching endothelial tubes. Dashed lines separate the Pecam1+ vessels in the septum from the Pecam1+ trabeculae. (E-H) Pictures of E12.5 Tnnt2Cre; Vegf-af/f (Vegf-a null) heart show no plexus formation in the peritruncal and septal myocardium. (I-K) Pictures of E14.5 control heart show the Pecam1+ coronary arteries (ca, arrows) and subepicardial vessels (arrowheads). (L-N) Pictures of E14.5 Vegf-a null heart show less and immaturely formed coronary arteries (arrows) but numerous and dilated subepicardial vessels (arrowheads). The null heart also has necrotic peritruncal and septal myocardium (L, arrows). Bar in I,L=100 μm; rest=20 μm.

DETAILED DESCRIPTION OF THE INVENTION

Figures 1A, 1B, 1C, 1D, 1E, 1F, 1G, 1H:
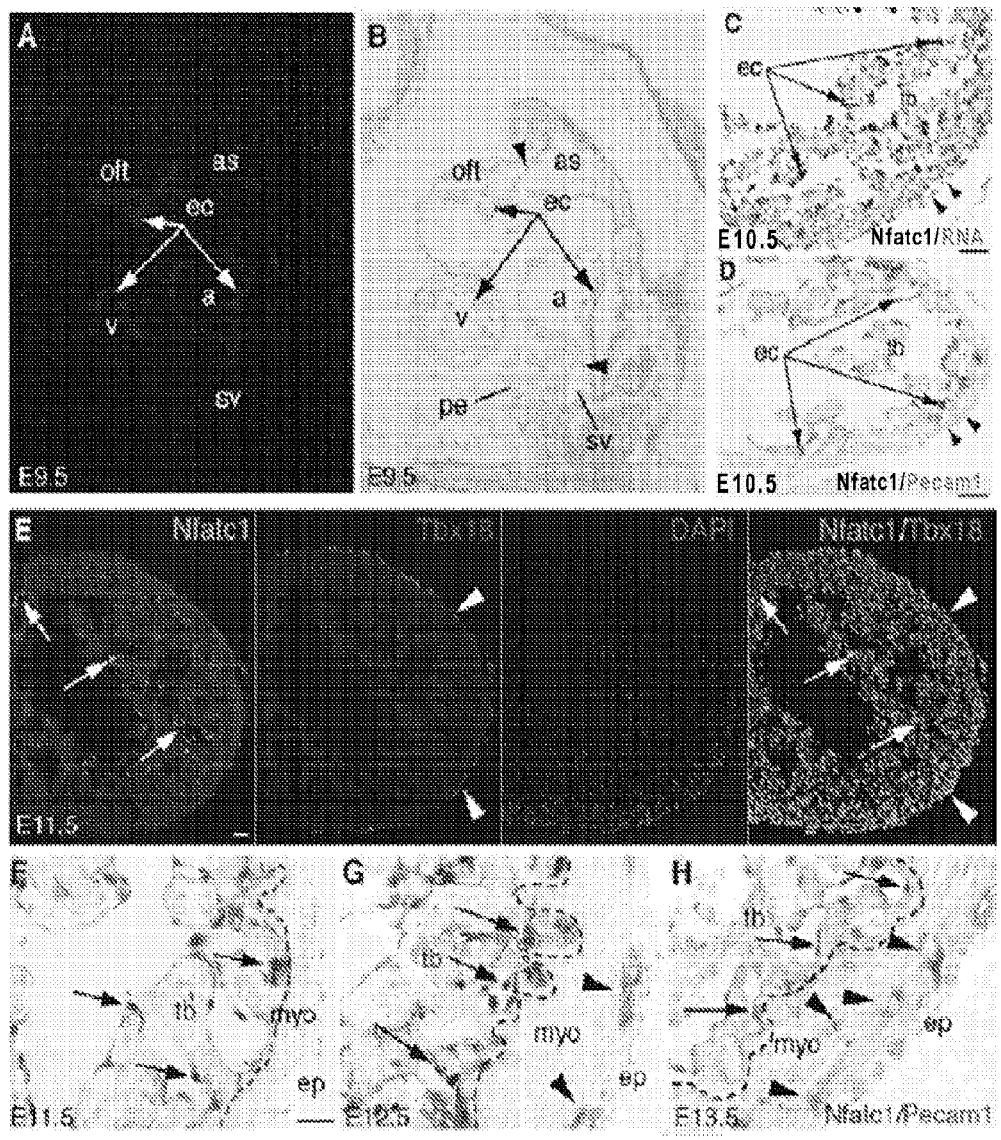
FIG. 1A-1H. In situ hybridization and immunochemistry show that Nfatc1 expression is restricted to the endocardium during coronary plexus formation (A,B) E9.5 heart sections show Nfatc1 transcripts in the endocardium (ec, arrows). Nfatc1 transcript signals separate the positive endocardium from the negative endothelium of aortic sac (as) and sinus venosus (sv) (arrowheads). Background signals are seen in the proepicardium (pe). a, atrium; oft, outflow tract; v, ventricle (C) E10.5 ventricular sections show Nfatc1 transcripts in the endocardium (arrows) but not epicardium (arrowheads). tb, trabeculae (D) E10.5 heart sections co-immunostained with antibodies against Nfatc1 (brown nuclear staining) and Pecam1 (red membrane staining) show Nfatc1 proteins in the endocardium (arrows) but not epicardium (arrowheads). (E) E11.5 heart sections show Nfatc1 proteins in the endocardium (arrows) but not in the Tbx18-positive epicardium (arrowheads). (F-H) E11.5-E13.5 heart sections stained with antibodies against Nfatc1 and Pecam1 show that Nfatc1 proteins are restricted to the endocardium (arrows). They are not present in the endothelium of coronary plexuses or Pecam1-positive cells in the myocardium (myo, arrowheads) or the mature coronary vessels. Dashed line separates the trabeculae from the compact wall. ep, epicardium. All bars=25 μm.

A method is provided for producing an artery-specific endothelial cell comprising contacting an Nuclear factor of activated T-cells, cytoplasmic 1 positive (Nfatc1+) endocardial cell, or contacting an inducible pluripotent stem cell in which Nfatc1+ has been induced, with an amount of an agent that activates vascular endothelial growth factor receptor-2 (Vegfr-2) effective to produce an artery-specific endothelial cell from the Nfatc1+ endocardial cell or inducible pluripotent stem cell.

In an embodiment, the artery-specific endothelial cell is an arteriolar endothelial cell. In an embodiment, the Nfatc1+ endocardial cell is isolated. In an embodiment, the Nfatc1+ endocardial cell is substantially pure. In an embodiment, the Nfatc1+ endocardial cell is human. In an embodiment, the inducible pluripotent stem cell in which Nfatc1+ has been induced is isolated. In an embodiment, the inducible pluripotent stem cell in which Nfatc1+ has been induced is substantially pure. In an embodiment, the inducible pluripotent stem cell in which Nfatc1+ has been induced is human. In an embodiment, the Nfatc1+ in the inducible pluripotent stem cell in which Nfatc1+ has been induced has been induced by artificial means, not naturally-occurring. In an embodiment, the artery-specific endothelial cell is a coronary artery-specific endothelial cell. In an embodiment, the Nfatc1+ endocardial cell is contacted with the agent that activates Vegfr-2. In an embodiment, the Nfatc1+ endocardial cell is contacted with an agent that activates human Vegfr-2. In an embodiment, the agent that activates Vegfr-2 is Vegf-a. In an embodiment, the Vegf-a is human Vegf-a. In an embodiment, the endocardial cell is obtained from a ventricular endocardium. In an embodiment, the endocardial cell is obtained from the ventricular endocardium of a subject being treated for a heart condition. In an embodiment, the cells are mammalian cells. In an embodiment, the cells are human cells. In an embodiment, the inducible pluripotent stem cell is not a derived from a human embryo.

A composition is provided comprising a plurality of isolated artery-specific endothelial cells produced by any of the instant methods. In an embodiment, the composition is 90% or greater isolated artery-specific endothelial cells. In an embodiment, the composition is 99% or greater isolated artery-specific endothelial cells. In an embodiment, the composition is 99.5% or greater isolated artery-specific endothelial cells. In an embodiment, the composition is 99.9% or greater isolated artery-specific endothelial cells. In an embodiment, the cell component of the composition is 90% or greater isolated artery-specific endothelial cells. In an embodiment, the cell component of the composition is 99% or greater isolated artery-specific endothelial cells. In an embodiment, the cell component of the composition is 99.5% or greater isolated artery-specific endothelial cells. In an embodiment, the cell component of the composition is 99.9% or greater isolated artery-specific endothelial cells. In an embodiment, the composition comprises a physiological carrier or a pharmaceutically acceptable carrier.

Also provided is a method of treating a heart condition in a mammalian subject comprising administering to the subject an amount of the artery-specific endothelial cells produced by any of the instant methods or an amount of any of the instant compositions effective to treat the heart condition in a mammalian subject. In an embodiment, a symptom of the heart condition is a diseased coronary artery of the heart. In an embodiment, the heart condition is atherosclerosis. In an embodiment, the heart condition is a heart infarction or is a coronary condition resulting from a heart infarction. In an embodiment the amount of artery-specific endothelial cells or an amount of the composition is administered into the bloodstream of the subject, for example, intravenously or intra-arterially. In an embodiment the amount of artery-specific endothelial cells or an amount of the composition is administered into a coronary artery of the subject. In an embodiment the amount of artery-specific endothelial cells or an amount of the composition is administered into the heart of the subject. In an embodiment, the subject is a human subject.

Also provided is a method of determining whether an agent specifically promotes the growth of coronary artery-specific endothelial cells comprising contacting an Nfatc1+ endocardial cell, or contacting an inducible pluripotent stem cell in which Nfatc1+ has been induced, with an amount of an activator of Vegfr-2 or of Vegf-a under conditions permitting the cell to produce an artery-specific endothelial cell from the inducible pluripotent stem cell or Nfatc1+ endocardial cell, and measuring the extent of growth of the artery-specific endothelial cell in the presence of, and in the absence of, the agent, wherein an increased growth of artery-specific endothelial cells in the presence of the agent as compared to in the absence of the agent indicates that the agent specifically promotes the growth of coronary artery-specific endothelial cells, and wherein a decreased, or no increase in, growth of artery-specific endothelial cells in the presence of the agent as compared to in the absence of the agent indicates that the agent does not specifically promote the growth of coronary artery-specific endothelial cells. In an embodiment, the agent is a small organic molecule, a peptide, an RNAi agent, a nucleic acid, an antibody or an antibody fragment. In an embodiment, the small organic molecule has a molecular mass of 2000 daltons or less. In an embodiment, the RNAi agent is an siRNA molecule or a shRNA molecule. In an embodiment, the antibody is isolated human, humanized or chimeric. In an embodiment, the antibody fragment is a fragment of an isolated human, humanized or chimeric antibody. In an embodiment, the antibody is monoclonal, or the fragment is a fragment of a monoclonal antibody. In an embodiment, the artery-specific endothelial cell is an arteriolar endothelial cell. In an embodiment, the Nfatc1+ endocardial cell is isolated. In an embodiment, the Nfatc1+ endocardial cell is substantially pure. In an embodiment, the Nfatc1+ endocardial cell is human. In an embodiment, the inducible pluripotent stem cell in which Nfatc1+ has been induced is isolated. In an embodiment, the inducible pluripotent stem cell in which Nfatc1+ has been induced is substantially pure. In an embodiment, the inducible pluripotent stem cell in which Nfatc1+ has been induced is human. In an embodiment, the Nfatc1+ in the inducible pluripotent stem cell in which Nfatc1+ has been induced has been induced by artificial means, not naturally-occurring.

Also provided is a method of treating a tumor in a subject comprising administering an inhibitor of Vegf-a or of Vegfr-2 to the subject in a manner permitting the inhibitor of Vegf-a or of Vegfr-2 to enter the tumor, thereby treating the tumor. In an embodiment, the inhibitor of Vegf-a or of Vegfr-2 inhibits angiogenesis in the tumor. In an embodiment, the inhibitor of Vegf-a is an antibody directed against Vegf-a, an antigen-binding fragment of an antibody directed against Vegf-a, a siRNA directed against a nucleic acid encoding Vegf-a, or an shRNA directed against a nucleic acid encoding Vegf-a. In an embodiment, the inhibitor of Vegfr-2 is an antibody directed against Vegfr-2, an antigen-binding fragment of an antibody directed against Vegfr-2, a siRNA directed against a nucleic acid encoding Vegfr-2, or an shRNA directed against a nucleic acid encoding Vegfr-2. In an embodiment, the inhibitor is a small organic molecule, a peptide, an RNAi agent, a nucleic acid, an isolated antibody or an isolated antibody fragment. In an embodiment, the small organic molecule has a molecular mass of 2000 daltons or less. In an embodiment, the RNAi agent is an siRNA molecule or a shRNA molecule directed against a nucleic acid encoding Vegf-a. In an embodiment, the RNAi agent is an siRNA molecule or a shRNA molecule directed against a nucleic acid encoding Vegfr-2. In an embodiment, the antibody is isolated human, humanized or chimeric. In an embodiment, the antibody fragment is a fragment of an isolated human, humanized or chimeric antibody. In an embodiment, the antibody is monoclonal, or the fragment is a fragment of a monoclonal antibody. In an embodiment the antibody or antibody fragment is directed against Vegfr-2. In an embodiment the Vegfr-2 is human Vegfr-2.

In an embodiment, the siRNA (small interfering RNA) as used in the methods or compositions described herein comprises a portion which is complementary to an mRNA sequence encoding Vegfr-2 or encoding Vegf-a, and the siRNA is effective to inhibit expression of Vegfr-2 or of Vegf-a. In an embodiment, the siRNA comprises a double-stranded portion (duplex). In an embodiment, the siRNA is 20-25 nucleotides in length. In an embodiment the siRNA comprises a 19-21 core RNA duplex with a one or 2 nucleotide 3' overhang on, independently, either one or both strands. In an embodiment, the overhang is UU. The siRNA can be 5' phosphorylated or not and may be modified with any of the known modifications in the art to improve efficacy and/or resistance to nuclease degradation. In a non-limiting embodiment, the siRNA can be administered such that it is transfected into one or more cells.

In one embodiment, a siRNA of the invention comprises a double-stranded RNA comprising a first and second strand, wherein one strand of the RNA is 80, 85, 90, 95 or 100% complementary to a portion of an RNA transcript of a gene encoding Vegfr-2 or encoding Vegf-a. Thus, in an embodiment, the invention encompasses an siRNA comprising a 19, 20 or 21 nucleotide first RNA strand which is 80, 85, 90, 95 or 100% complementary to a 19, 20 or 21 nucleotide portion, respectively, of an RNA transcript of a gene encoding Vegfr-2 or encoding Vegf-a. In embodiment, the second RNA strand of the double-stranded RNA is also 19, 20 or 21 nucleotides, respectively, a 100% complementary to the first strand. In another embodiment, a siRNA of the invention comprises a double-stranded RNA wherein one strand of the RNA comprises a portion having a sequence the same as a portion of 18-25 consecutive nucleotides of an RNA transcript of a gene encoding encoding Vegfr-2 or encoding Vegf-a. In yet another embodiment, a siRNA of the invention comprises a double-stranded RNA wherein both strands of RNA are connected by a non-nucleotide linker. Alternately, a siRNA of the invention comprises a double-stranded RNA wherein both strands of RNA are connected by a nucleotide linker, such as a loop or stem loop structure.

In one embodiment, a single strand component of a siRNA of the invention is from 14 to 50 nucleotides in length. In another embodiment, a single strand component of a siRNA of the invention is 14, 15, 16, 17, 18, 19, 20, 21, 22, 23, 24, 25, 26, 27, or 28 nucleotides in length. In yet another embodiment, a single strand component of a siRNA of the invention is 21 nucleotides in length. In yet another embodiment, a single strand component of a siRNA of the invention is 22 nucleotides in length. In yet another embodiment, a single strand component of a siRNA of the invention is 23 nucleotides in length. In one embodiment, a siRNA of the invention is from 28 to 56 nucleotides in length.

In another embodiment, an siRNA of the invention comprises at least one 2'-sugar modification. In another embodiment, an siRNA of the invention comprises at least one nucleic acid base modification. In another embodiment, an siRNA of the invention comprises at least one phosphate backbone modification.

In one embodiment, RNAi inhibition of Vegfr-2 or Vegf-a is effected by a short hairpin RNA ("shRNA"). The shRNA is introduced into the cell by transduction with a vector. In an embodiment, the vector is a lentiviral vector. In an embodiment, the vector comprises a promoter. In an embodiment, the promoter is a U6 or H1 promoter. In an embodiment the shRNA encoded by the vector is a first nucleotide sequence ranging from 19-29 nucleotides complementary to the target gene, in the present case encoding Vegfr-2 or encoding Vegf-a. In an embodiment the shRNA encoded by the vector also comprises a short spacer of 4-15 nucleotides (a loop, which does not hybridize) and a 19-29 nucleotide sequence that is a reverse complement of the first nucleotide sequence. In an embodiment the siRNA resulting from intracellular processing of the shRNA has overhangs of 1 or 2 nucleotides. In an embodiment the siRNA resulting from intracellular processing of the shRNA overhangs has two 3' overhangs. In an embodiment the overhangs are UU.

In an embodiment the Vegf-a is a human Vegf-a. Exemplary human Vegf-a protein sequences comprise Genbank: AAH65522.2 and GenBank: AAH11177.2, and the nucleic acids encoding all of or encoding the non-precursor part of such are encompassed.

In an embodiment the Vegfr-2 is a human Vegfr-2. Exemplary human Vegfr-2 protein sequences comprise UniProtKB/Swiss-Prot: P35968.2 and NCBI Reference Sequence: NP_002244.1, and the nucleic acids encoding all of or encoding the non-precursor part of such are encompassed.

The term "tumor," as used herein, refers to all neoplastic cell growth and proliferation, whether malignant or benign, and all pre-cancerous and cancerous cells and tissues, which has a blood supply.

As used herein, "treating" a tumor means that one or more symptoms of the disease, such as the tumor itself, vascularization of the tumor, or other parameters by which the disease is characterized, are reduced, ameliorated, prevented, placed in a state of remission, or maintained in a state of remission. "Treating" a tumor also means that one or more hallmarks of the tumor may be eliminated, reduced or prevented by the treatment. Non-limiting examples of such hallmarks include uncontrolled degradation of the basement membrane and proximal extracellular matrix, migration, division, and organization of the endothelial cells into new functioning capillaries, and the persistence of such functioning capillaries. In an embodiment, the method inhibits angiogenesis in the tumor.

The phrase "and/or" as used herein, with option A and/or option B for example, encompasses the individual embodiments of (i) option A alone, (ii) option B alone, and (iii) option A plus option B.

It is understood that wherever embodiments are described herein with the language "comprising," otherwise analogous embodiments described in terms of "consisting of" and/or "consisting essentially of" are also provided.

Where aspects or embodiments of the invention are described in terms of a Markush group or other grouping of alternatives, the present invention encompasses not only the entire group listed as a whole, but each member of the group subjectively and all possible subgroups of the main group, but also the main group absent one or more of the group members. The present invention also envisages the explicit exclusion of one or more of any of the Markush group members in the claimed invention.

All combinations of the various elements described herein are within the scope of the invention unless otherwise indicated herein or otherwise clearly contradicted by context.

In the event that one or more of the literature and similar materials incorporated by reference herein differs from or contradicts this application, including but not limited to defined terms, term usage, described techniques, or the like, this application controls.

This invention will be better understood from the Experimental Details, which follow. However, one skilled in the art will readily appreciate that the specific methods and results discussed are merely illustrative of the invention as described more fully in the claims that follow thereafter.

Experimental Details

Here it is disclosed that ventricular endocardial cells are a major origin of coronary artery endothelium. Myocardial Vegf-a to endocardial Vegfr-2 signaling is required for these cells to differentiate into coronary endothelium. This knowledge provides better engineering for coronary artery regeneration.

The origins and developmental mechanisms of coronary arteries are incompletely understood. Here it is shown by fate mapping, clonal analysis and immunohistochemistry that endocardial cells generate the endothelium of coronary arteries. Dye tracking, live imaging, and tissue transplantation also revealed that ventricular endocardial cells are not terminally differentiated; instead, they are angiogenic and form coronary endothelial networks. Myocardial Vegf-a or endocardial Vegfr-2 deletion inhibited coronary angiogenesis and arterial formation by ventricular endocardial cells. In contrast, lineage and knockout studies showed that endocardial cells make a small contribution to the coronary veins, the formation of which is independent of myocardial-to-endocardial Vegf signaling. Thus, contrary to the current view of a common source for the coronary vessels, the findings indicate that the coronary arteries and veins have distinct origins and are formed by different mechanisms.

Results

Characterization of Nfatc1 expression during coronary vessel development: Cardiac endocardial cells comprise a unique endothelial cell population that expresses Nfatc1 during development, while vascular endothelial cells do not express Nfatc1 (Chang et al., 2004; de la Pompa et al., 1998; Ranger et al., 1998; Zhou et al., 2005). In this study, Nfatc1 expression in embryonic tissues was further characterized relative to coronary development. It was confirmed by in situ hybridization that Nfatc1 transcripts demarcated endocardium at embryonic day (E) 9.5, since the endothelium of aortic sac, sinus venosus, and the rest of the peripheral vasculature was negative for Nfatc1 transcripts (FIG. 1A, 1B). Nfatc1 transcripts were not found in the proepicardium either. At E10.5 Nfatc1 transcripts were similarly restricted to the endocardium (FIG. 1C). Likewise, double immunostaining of Nfatc1 and Pecam1 (pan-endothelial marker) revealed that Nfatc1 proteins were confined to the endocardium (FIG. 1D). Neither Nfatc1 transcripts nor proteins were detected in the forming epicardium. Furthermore, co-immunostaining of Nfatc1 and Tbx18 (epicardial marker) (Kraus et al., 2001) confirmed that epicardial cells did not express Nfatc1 at E11.5 (FIG. 1E).

When coronary plexuses developed from E11.5 to E13.5, Nfatc1 transcripts were downregulated in the ventricular endocardium (data not shown) while Nfatc1 proteins remained in a subset of endocardial cells (FIG. 1F-1H). Neither Nfatc1 transcripts (data not shown) nor Nfatc1 proteins were found in the endothelium of coronary plexuses (FIG. 1G, 1H). Likewise, the endothelium of developed coronary vessels from E14.5 to E16.5 did not have detectable Nfatc1 transcripts or Nfatc1 proteins, which were found only in the valve endocardium. These findings showed that Nfatc1 expression is restricted to the endocardium during coronary development. Nfatc1 is not expressed in the proepicardium/epicardium, sinus venosus, or developing coronary vessels.

Nfatc1+ endocardial precursors generate coronary plexuses: To study the developmental fate and function of endocardial cells, a Cre knock-in mouse strain was generated, Nfatc1Cre, in which Cre cDNA with an internal ribosomal entry site was inserted downstream of the stop codon of the mouse Nfatc1 (Zhou et al., 2002). Nfatc1Cre mice developed normally and bred to the RCEfsEGFP (Miyoshi et al., 2010; Sousa et al., 2009) or R26fslz mice (Soriano, 1999). Cre expression was restricted to the endocardium of Nfatc1Cre embryos; no expression was seen in the sinus venosus, liver, pharyngeal arch, proepicardium/epicardium, myocardium at E9.5-E10.5, or developing coronary vessels (data not shown).

The fate of endocardial cells was then tracked by the inherited expression of enhanced green fluorescent protein (EGFP) or beta-galactosidase (b-gal hereafter). Nfatc1Cre-mediated EGFP expression began at E9.0 in the endocardium of Nfatc1Cre;RCEfsEGFP embryos. At E10.5, EGFP expression was limited to the heart proper of Nfatc1Cre;

RCEfsEGFP embryos. Sectional examination of E9.5-E10.5 Nfatc1Cre;RCEfslz embryos confirmed restricted b-gal expression in the endocardium and in the cushion mesenchyme derived from endocardial cells. Neither Cre reporter gene was expressed in the proepicardium/epicardium, myocardium, pharyngeal arch, and liver bud.

Figures 2A, 2B, 2C, 2D, 2E, 2F, 2G, 2H, 2I, 2J, 2K, 2L, 2M:
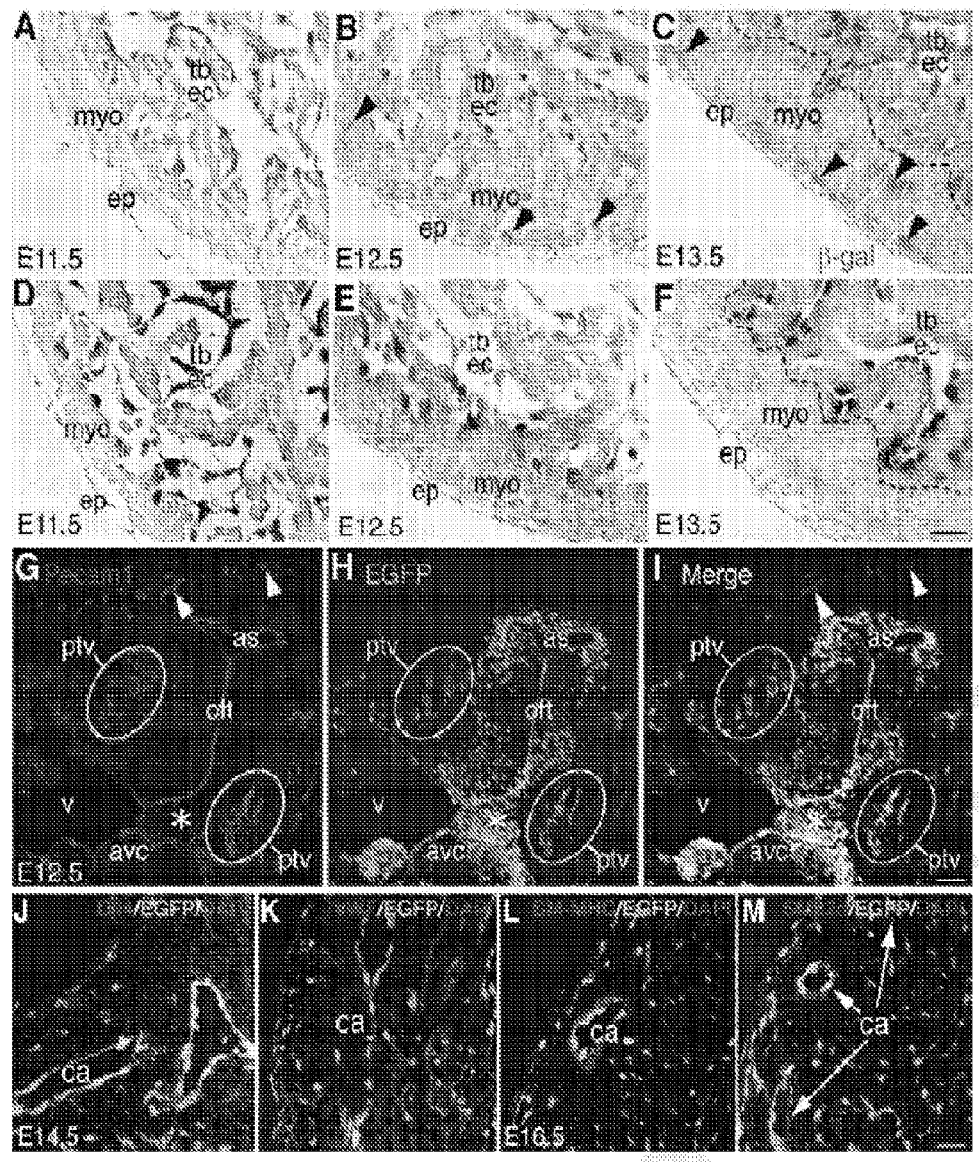
FIG. 2A-2M. Fate-mapping analysis reveals that Nfatc1+ endocardial cells generate coronary vascular endothelium (A-C) X-gal stained E11.5-E13.5 heart sections of Nfatc1Cre;R26fslz embryos show that the b-gal tagged Nfatc1+ endocardial cells reside in the endocardium of the myocardial wall and trabeculae at E11.5 (A), they begin to invade the myocardium at E12.5 (B, arrowheads) and generate networks of coronary plexuses at E13.5 (C, arrowheads). The descendants of Nfatc1+ cells are not present in the epicardium and myocardium. (D-F) X-gal stained E11.5-E13.5 heart sections of control Nfatc1lacZ-BAC embryos show that the b-gal activities directed by the Nfatc1 promoter/enhancer are restricted to the endocardium and not present in the myocardium and epicardium. Unlike Nfatc1Cre, Nfatc1lacZ does not label the coronary plexuses. (G-I) Dual fluorescent sections through ventricular (v) outflow tract (oft) of E12.5 Nfatc1Cre;RCEfsEGFP embryos show the EGFP+ endothelial descendants of Nfatc1+ endocardial cells in the Pecam1+ coronary plexuses in the peritruncal region (ptv). The peripheral vessels (arrowheads) expressing Pecam1 but not EGFP are not derived from the Nfatc1+ endocardial cells. Mesenchyme of atrioventricular canal (avc, asterisk), derived from the cushion endocardial cells, is EGFP positive but Pecam1 negative. (J-K) Dual fluorescent sections of E14.5 Nfatc1Cre;RCEfsEGFP heart show EGFP+ endothelial descendants of endocardial cells in the Dll4+ or vWF+ endothelium (red) of the main coronary arteries (ca). The trabecular endocardium is negative for vWF. (L-M) Dual fluorescent sections of E16.5 Nfatc1Cre; RCEfsEGFP heart show EGFP+ endothelial descendants of endocardial cells in the inner layer of the coronary arteries (ca) surrounded by smooth muscle cells positive for SM-MHC or SM22a. All Bars=25 μm.

Although Nfatc1 expression was not found in the sinus venous endothelium, Nfatc1Cre-mediated b-gal or EGFP expression was observed in some sinus venous endothelial cells at E10.5-E11.5, suggesting that Nfatc1+ endocardial cells contribute to a subset of sinus venous endothelial population. The lineage contribution was then examined of endocardial cells to coronary vessels in Nfatc1Cre;R26fslz embryos and it was found that cells of the emerging coronary plexuses at E11.5-E13.5 uniformly expressed b-gal (FIG. 2). The b-gal+ cells, derived from the Nfatc1+ precursors at E11.5, invaded the myocardium at E12.5 and formed coronary plexuses throughout the myocardium at E13.5 (FIG. 2C).

Conversely, in control Nfatc1lacZ-BAC embryos that expressed b-gal driven by the Nfatc1 promoter/enhancer (Misfeldt et al., 2009), b-gal expression (an indicator of the Nfatc1Cre activities) was restricted to the endocardium and absent in coronary plexuses (FIG. 2D-2F). This observation is consistent with the finding that coronary plexuses do not express Nfatc1 at these stages, thus further eliminating the possibility of ectopic Cre expression in coronary plexuses.

To verify the cell identity of the endocardial-derived coronary cells, the EGFP+ descendants of Nfatc1+ endocardial cells were co-labeled with Pecam1 antibodies in Nfatc1Cre;RCEfsEGFP embryos. It was found that most Pecam1-positive cells in the peritruncal coronary vessels expressed EGFP at E12.5, whereas the vessels outside the heart were labeled only by Pecam1 antibodies (FIG. 2G-2I). Also, all coronary plexuses arising at E11.5-E13.5 in the ventricular wall co-expressed Pecam1 and EGFP. E14.5 or E16.5 Nfatc1Cre;RCEfsEGFP heart sections were then stained with multiple cardiovascular markers and it was found that the EGFP+ descendants of Nfatc1+ endocardial cells were present in the endothelium of coronary arteries expressing arterial endothelial markers Dll4 (FIG. 2J), Ephb2 and Jagged1 (data not shown). It was also noted that while endocardial cells were negative for vWF, their descendants in coronary arteries acquired vWF expression (FIG. 2K). Thus, the acquisition of vWF and loss of Nfatc1 expression in coronary endothelial cells may serve as makers for endocardial to coronary endothelial differentiation. Further staining of smooth muscle myosin heavy chain (SM-MHC) and $SM22_1$ showed that the EGFP+ endocardial descendants contributed to the endothelium of developed coronary arteries, but they did not become vascular smooth muscle cells of the cognate vessels (FIG. 2L, 2M). In contrast to their prominent arterial presence, few EGFP+ descendants of endocardial cells were found in coronary veins. EGFP+ descendants were also absent in lymphatic vessels and did not become cardiomyocytes.

The fate mapping of Nfatc1Cre-marked endocardial cells in coronary vessels was further compared to that of Tie1Cre-labeled pan-endothelial (arterial and venous) cells (Gustafsson et al., 2001). Unlike Tie1+ endothelial descendants which formed vascular networks on the surface of E14.5 hearts, Nfatc1+ endocardial descendants did not form the networks but contributed to the intramyocardial vessels. Pecam1 staining of E16.5 Nfatc1Cre;RCEfsEGFP hearts confirmed that Nfatc1+ endocardial descendants contributed to most intramyocardial vessels (including the main arteries), with much less presence in the subepicardial vessels.

Coronary arteriograms of E16.5 Nfatc1Cre;RCEfsEGFP hearts validated that EGFP+ descendants of Nfatc1+ endocardial cells contributed to the entire coronary artery network, including the main coronary arteries and their branches, arterioles, and capillaries.

Quantitative analysis of Nfatc1+ endocardial descendants in the coronary vessels of E16.5 hearts showed that they contributed to 72%, 81%, or 37% endothelial population of major coronary arteries, intramyocardial, or subepicardial vessels, respectively. These findings establish that endocardial cells are a major source of endothelial cells of the intramyocardial vessels including major coronary arteries and suggest that the majority of subepicardial vascular endothelium arises from a different origin.

Figures 3A, 3B, 3C, 3D, 3E, 3F, 3G, 3H:
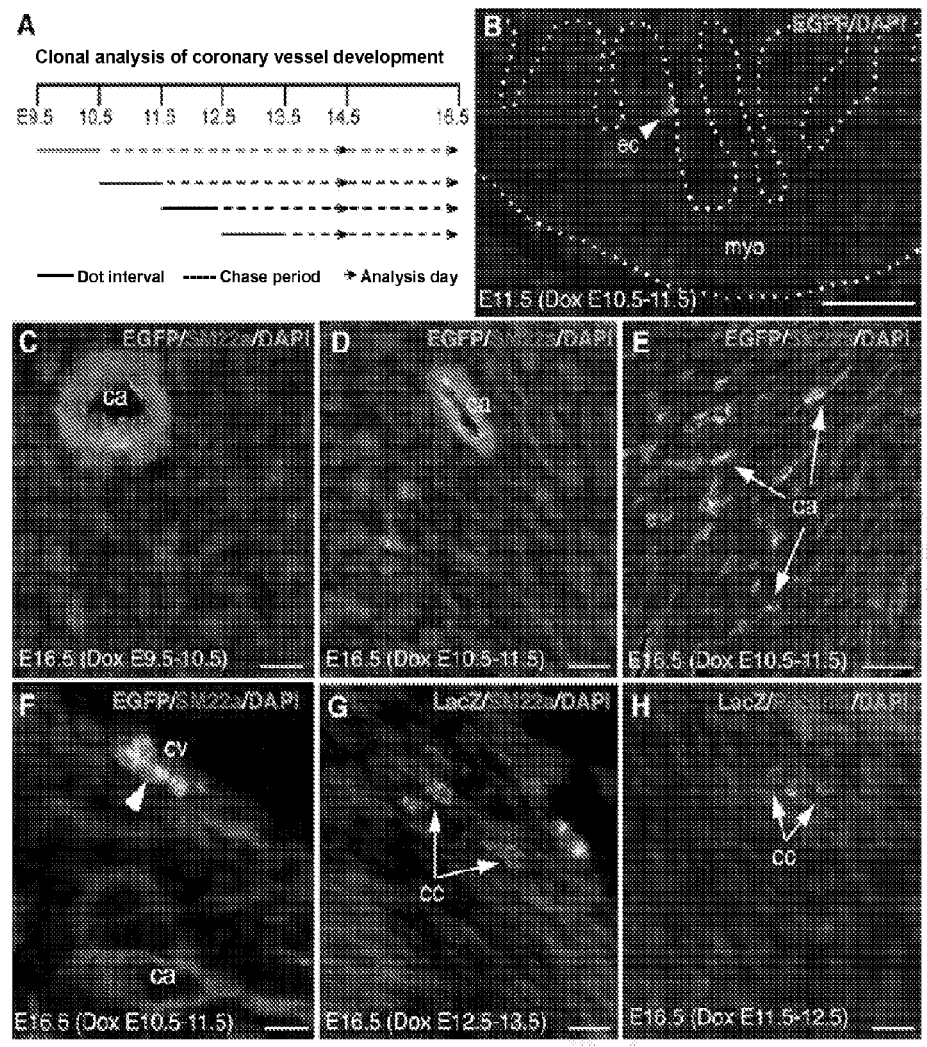
FIG. 3A-3H. Clonal analysis of coronary development shows the descendants of Nfatc1+ endocardial cells in the coronary vascular endothelium (A) A schematic diagram showing clonal analysis of coronary development using the Nfatc1nrtTA;tetO-Cre system induced by doxycycline (Dox). (B) Heart section of Nfatc1nrtTA;tetO-Cre;RCEfsEGFP E11.5 embryo induced at E10.5 with a limited Dox dose shows single EGFP-labeled cells in the endocardium (arrowhead) (see also Figure S7). (C-E) Sections of E16.5 Nfatc1nrtTA;tetO-Cre;RCEfsEGFP heart induced at E9.5 (C) or E10.5 (D,E) show the EGFP+ cell clusters in the large (C, D) or small coronary arteries (arrows) expressing SM22a. (F) Sections of E16.5 Nfatc1nrtTA;tetO-Cre;RCEfsEGFP heart induced at E10.5 shows the EGFP+ cell clusters (arrowhead) in the subepicardial vessels alongside the SM22a+ cells. (G) Sections of E16.5 Nfatc1nrtTA;tetO-Cre; R26fslz heart induced at E12.5 shows the LacZ-labeled capillary cells (cc) cluster (green; arrows) alongside the SM22a expressing small arteries (red). (H) Sections of E16.5 Nfatc1nrtTA;tetO-Cre;R26fslz heart induced at E11.5 shows the LacZ+ capillary cells cluster (arrows) alongside the Pecam1+ small vessels (red). All bars=20 μm.

Clonal analysis establishes spatiotemporal differentiation of endocardial cells into coronary endothelial cells: To confirm that the endocardium is a major source of coronary arterial endothelial cells and determine when endocardial cells are committed to a coronary endothelial fate, we generated Nfatc1nrtTA-BAC mice using an Nfatc1-BAC DNA, and bred them to tetO-Cre;RCEfsEGFP or tetO-Cre; R26fslz mice. When induced with doxycycline (Dox) at E7.5-E11.5, the tetO-Cre-mediated EGFP expression was found to mark endocardial cells and their mesenchymal descendants. Limited Dox dose was then applied for 24 hours, at E9.5, E10.5, E11.5, or E12.5 (FIG. 3A), to induce rare recombination events in individual cells in the endocardium (FIG. 3B). The expansion of EGFP+ or b-gal+ single cells were chased for 1-7 days until E14.5 or E16.5, and the clonality and coronary location of cell clusters were determined by expression of the reporters, vascular markers, and histology. A total of 39 whole hearts were analyzed by evaluating serial sections (FIG. 3C-3H). Single or separated EGFP+ or b-gal+ cell clusters were found in the endothelium of major or small coronary arteries (FIG. 3C-3E), veins (FIG. 3F), or capillaries (FIG. 3G, 3H). Some cells near developing arteries exhibited filopodia, suggesting that they were migrating cells. Cell clusters were also found in heart valves. However, they were not detected in the sinus venosus. Quantitative analysis of clones showed that over 86% of the Nfatc1+ endothelial descendants that derived at E9.5-E13.5 were in the intramyocardial vessels at E14.5 or E16.5; the remainders were in the subepicardial vessels. The endocardial precursors labeled around E11.5 generated most coronary endothelial cells; their ability to differentiate into endothelial cells was greatly reduced after E12.5.

Consistent with their predominant presence in the endothelium of intramyocardial vessels, the number of Nfatc1+ endothelial descendants found in the main coronary arteries at E14.5 or E16.5 was 13 or 5 times greater than that in the main veins. Furthermore, the numbers of labeled endocardial cells across the 39 analyzed hearts correlated significantly with the numbers of their sister endothelial cells in both intramyocardial and subepicardial vessels. However, the correlation between the endocardial and intramyocardial numbers (Pearson's correlation coefficient r=0.86, p=$4.0\times10^{-12}$) was higher than that between the endocardial and subepicardial numbers (r=0.59, p=$8.2\times10^{-5}$).

Thus, clonal analysis suggests that endocardial cells commit to a coronary endothelial fate right before coronary plexus formation and supports the conclusion from the Nfatc1Cre fate mapping that the endocardium is a major source of the endothelium of intramyocardial vessels and major coronary arteries.

Ventricular endocardial cells form coronary plexuses by angiogenesis: To visualize how ventricular endocardial cells generated coronary plexuses, hearts were isolated from E10.5 or E11.5 embryos and labeled endocardial cells with Red Fluorescent CMTPX. The ventricles were used in a Matrigel endothelial tube assay. Single labeled endocardial cells were found that had migrated through the myocardial wall into Matrigel in the presence of Vegf120. When using the red dye to label Nfatc1Cre;RCEfsEGFP embryonic ventricles, dye-labeled individual cells were observed integrated into an endothelial network generated by EGFP+ descendants of Nfatc1+ ventricular endocardial cells (FIG. 4, A-C).

Figures 4A, 4B, 4C, 4D, 4E, 4F, 4G, 4H, 4I, 4J, 4K, 4L:
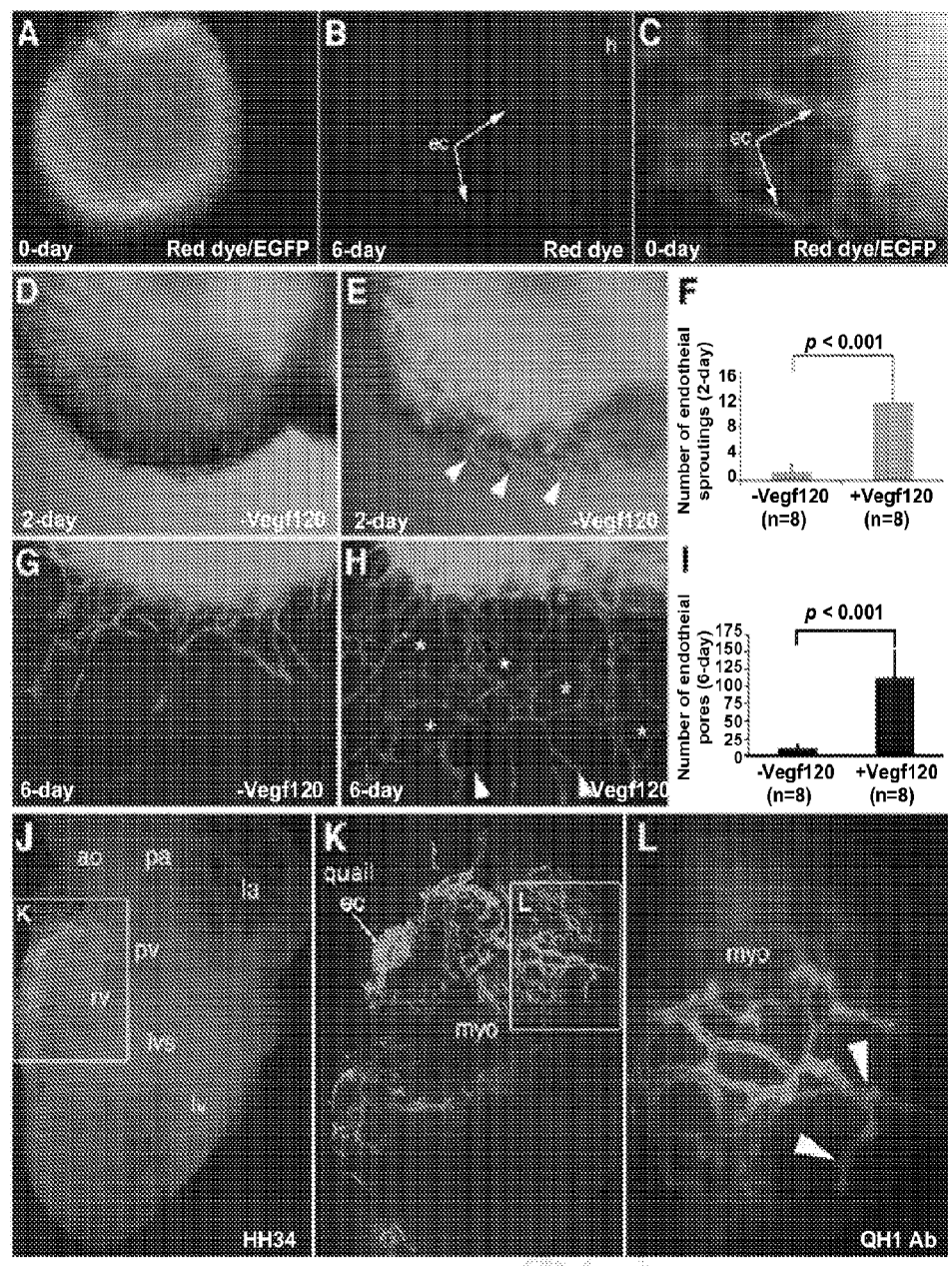
FIG. 4A-4L. Dye labeling, ventricular explant culture and tissue transplantation show that ventricular endocardial cells form the vascular plexus by angiogenesis (A-C) Dye labeling and explant matrigel cultures using ventricles from E11.5 Nfatc1Cre;RCEfsEGFP hearts (h) show red fluorescent CMTPXlabeled individual endocardial cells (arrows) that had migrated through the ventricular wall and integrated into an EGFP+ endothelial network upon Vegf120 treatment. (D-I) Matrigel angiogenesis assays show that Vegf120 significantly promotes transmural migration, sprouting (arrowheads), and endothelial networking (asterisks) by Nfatc1+ descendants. The error bars represent SD. (J-L) Images of QH1 antibody stained HH34 quail-chick chimerical heart sliced through the right ventricle at the implanted site show that the QH1+ descendants of engrafted HH15 quail endocardial cells invade chick myocardium and generate intramyocardial vessels. Quail endocardial cells, implanted at the surface of the atrioventricular junction of the chick heart (K), generate intensive myocardial vascular networks by angiogenic sprouting and branching (L, arrowheads).

The angiogenic function of endocardial cells was further characterized by time-lapse fluorescence live imaging and quantified. Without Vegf120, Nfatc1+ precursors invaded the ventricular wall and sprouted to form endothelial tubes, which then fused into distinct vessels in the myocardium. With Vegf120, the Nfatc1+ precursors readily migrated through the ventricular wall and underwent angiogenic sprouting (FIG. 4D, 4E). Within 6 days of Vegf120 exposure, the descendants of Nfatc1+ precursors generated sophisticated endothelial networks (FIG. 4G, 4H). In contrast, angiogenic sprouting and networking were significantly limited without Vegf120 (FIG. 4F, 4I). Besides Vegf120, other Vegf-a isoforms such as Vegf164 and Vegf188 were capable of promoting coronary angiogenesis, whereas Vegf-c, Vegf-d, Fgf2, and Fgf9 had partial or no effects (data not shown). These data showed that endocardial cells can develop into coronary endothelial networks and suggested that Vegf-a is a major factor involved in coronary plexus formation by ventricular endocardial cells.

To further test coronary angiogenesis by ventricular endocardial cells, quail-to-chick transplantation experiments were conducted in which ventricular endocardium or proepicardium from quail embryonic hearts was isolated at the Hamburger and Hamilton (HH) stage 15 (prior to coronary plexus formation) and implanted at the inner curvature of the atrioventricular junction of HH15 chick embryonic hearts. Using the QH1 antibody that labels quail, but not host chick, endothelial cells, we detected the contribution of implanted quail cells to coronary arteries of chick hearts at HH34. Quail endocardial cells invaded chick ventricular wall and developed into an extensive endothelial network in the myocardium (FIG. 4J-4L), while quail proepicardium largely generated subepicardial vessels.

Together, the results from four distinct experimental approaches (Nfatc1Cre fatemapping, clonal analysis, dye labeling, and cross-species transplantation) all demonstrate that ventricular endocardial cells generate endothelial cells of coronary arteries. The endocardial descendants comprise the majority of endothelial cells in intramyocardial vessels and coronary arteries. They further show that endocardial cells are not terminally differentiated; they are angiogenic and are activated by Vegf-a to generate coronary plexuses.

Figures 5A, 5N:
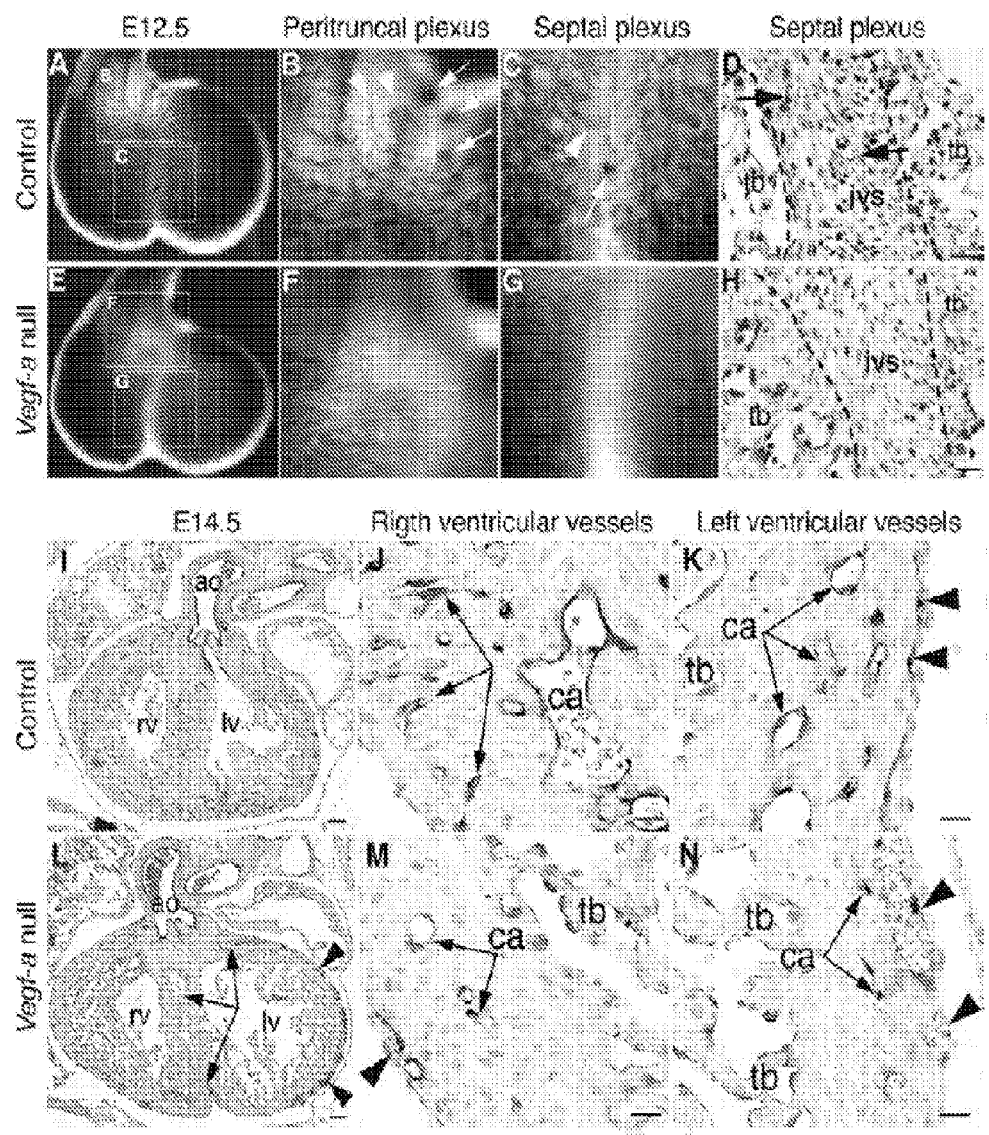

Myocardial Vegf-a is required for coronary angiogenesis and artery formation: Vegf-a is known to be produced by the developing myocardium (Giordano et al., 2001; Miquerol et al., 2000; Tomanek et al., 2006) and required for vasculogenesis and angiogenesis in development (Carmeliet et al., 1996; Ferrara et al., 1996). Therefore, it was asked if myocardial Vegf-a was necessary in vivo for endocardial cells to differentiate into coronary endothelial cells and form coronary arteries. The Tnnt2 promoter-Cre (Tnnt2Cre) (Chen et al., 2006; Jiao et al., 2003) and Vegf-af/f mice (Gerber et al., 1999) were used to disrupt Vegf-a in the myocardium (data not shown). Wholemount or sectional Pecam1 staining of E12.5 Tnnt2Cre;Vegf-a+/+ (Control) and Tnnt2Cre;Vegf-af/f (Vegf-a null) hearts showed that angiogenic sprouts or coronary plexuses were present in the peritruncal area or ventricular septum of control (FIG. 5, A-D) but not Vegf-a null hearts (FIG. 5, E-H). Thus myocardial Vegf-a is necessary for coronary plexus formation.

From E12.5 to E13.5 when coronary plexuses had developed into a well-organized intramyocardial endothelial network in control hearts, the angiogenic defect persisted in all Vegf-a null hearts leading to myocardial necrosis. By E14.5 when control hearts developed intramyocardial coronary arteries and subepicardial veins with distinct patterns (FIG. 5, I-K), Vegf-a null hearts had only few immature myocardial coronary arteries and developed dilated subepicardial veins (FIG. 5, L-N). Quantitative analysis confirmed an 88% reduction in the number of Pecam1+ intramyocardial endothelial cells in E14.5 Vegf-a null hearts, but only a 37% decrease in the subepicardial endothelial cells. These findings indicated that myocardial Vegf-a triggers coronary angiogenesis and is required for arterial formation. The fact that coronary veins formed indicated that they have an embryonic origin independent of myocardial Vegf-a, although the vein defect might be a consequence of myocardial Vegf-a deficiency and/or they might be secondary to the arterial defect.

Vegf-a null hearts also exhibited cardiac phenotypes, including thin ventricular walls, necrotic septa, cardiac hemorrhages, and ruptured septa at E15.5. All Vegf-a null embryos were runted and died after E15.5. To rule out early myocardial defects that might affect coronary angiogenesis, myocardial function and structure was examined, but no myocardial apoptosis, abnormal cardiac gene expression, and alterations in the ultrastructure of sarcomeres, mitochondria, or Golgi apparatus in E11.5-E12.5 Vegf-a null hearts was found (data not shown).

Figures 6A, 6N:
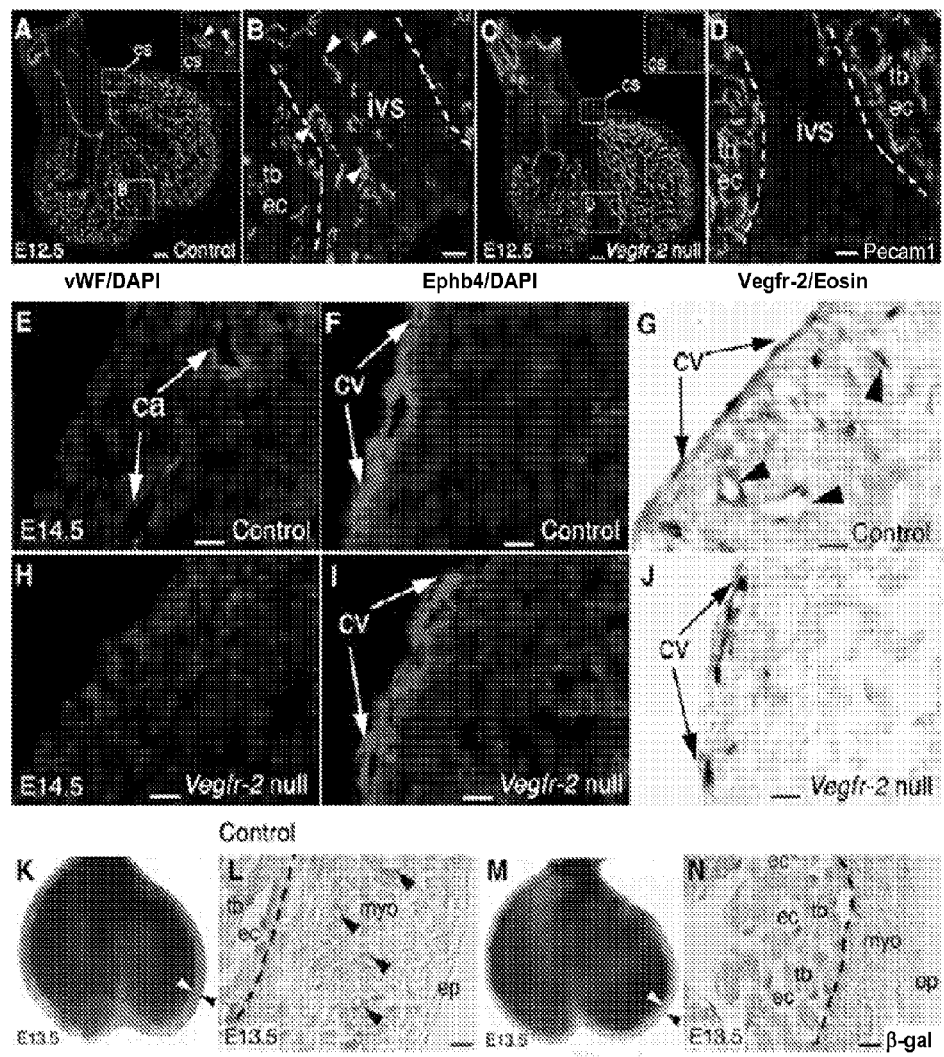
FIG. 6A-6N. Disruption of Vegfr-2 in the endocardium shows that endocardial Vegfr-2 is required for coronary angiogenesis and artery formation by endocardial cells (A,B) E12.5 Nfatc1Cre;Vegfr-2+/+ (Control) heart sections stained with Pecam1 antibodies show coronary endothelial tubes in the myocardium of the coronary sulcus (cs) (A, inset) and interventricular septum (B, arrowheads). (C,D) E12.5 Nfatc1Cre;Vegfr-2f/f (Vegfr-2 null) heart sections stained with Pecam1 antibodies show no coronary endothelial tubes in the coronary sulcus (C, inset) and interventricular septum (D). Dashed lines separate the septum from the Pecam1+ endocardium of trabeculae. (E-G) E14.5 control heart sections show that mature coronary arteries are positive for vWF staining (E, arrows) while subepicardial coronary veins (cv) are positive for Ephb4 staining (F, arrows). Vegfr-2 proteins are present in arteries (G, arrowheads) and veins (G, arrows). (H-J) E14.5 Vegfr-2 null heart sections show no vWF+ coronary arteries in the myocardium (H), but presence of Ephb4+ subepicardial coronary veins (I, arrows). Vegfr-2 proteins are only present in the coronary veins (J, arrows). (K,L) X-gal stained E13.5 Nfatc1Cre; Vegfr-2+/+;R26fslz (Control) heart show that the b-gal+ descendants of Nfatc1+ endocardial cells generate the coronary vessels in the ventricular wall (arrowheads). Dashed lines distinguish the b-gal+ coronary plexuses in the compact wall from the b-gal+ endocardium of trabeculae. (M,N) X-gal stained E13.5 Nfatc1Cre;Vegfr-2f/f;R26fslz (Vegfr-2 null) heart show no b-gal+ coronary plexuses derived from endocardial cells in the ventricular wall. Bar in A,C=100 µm; rest=20 µm.

These results suggest that the cardiac phenotypes are a result of the vascular defects. Endocardial Vegfr-2 is required for coronary angiogenesis and artery formation Vegfr-2 is a major Vegf receptor required for vessel formation during development (Shalaby et al., 1995). It was investigated if Vegfr-2 could transduce Vegf-a signals to trigger coronary angiogenesis by Nfatc1+ endocardial cells. Nfatc1Cre and Vegfr-2f/f (Haigh et al., 2003) were used to remove Vegfr-2 in the endocardium. Vegfr-2 antibody staining of E10.5 Vegfr-2+/+;Nfatc1Cre (Control) and Vegfr-2f/f;Nfatc1Cre embryos (Vegfr-2 null) showed that the deletion was restricted to the endocardium, whereas Vegfr-2 expression in the vasculature outside the heart was not affected. Similar to E12.5 Vegf-a null embryos, E12.5 Vegfr-2 null embryos did not develop coronary plexuses in the peritruncal/coronary sulcus area or ventricular septum (FIG. 6, A,B vs. C,D). The early angiogenic defect resulted in severely diminished or no coronary arteries in all E14.5 Vegfr-2 null embryos (FIG. 6, E vs. H). In contrast, coronary veins developed in these embryos (FIG. 6, F vs. I). The arterial specific defect was consistent with Vegfr-2 deletion in the Nfatc1+ endocardial precursors, as Vegfr-2 expression in the endothelium of coronary veins was not affected (FIG. 6, G vs. J).

Like Vegf-a null embryos, all Vegfr-2 null embryos developed cardiac hemorrhages by E14.5, they were runted thereafter, and died in utero. Quantitative analysis of immunostaining confirmed a 74% reduction in the number of Pecam1+ intramyocardial endothelial cells in E14.5 Vegfr-2 null hearts and only a 24% decrease in subepicardial endothelial cells. These results demonstrate that Vegfr-2 function is necessary for differentiation of endocardial cells into endothelial cells to form coronary arteries.

To track the fate of Vegfr-2 null endocardial cells during coronary angiogenesis, we generated Nfatc1Cre;Vegfr-2f/f; R26fslz and Nfatc1Cre;Vegfr-2f/f;RCEfsEGFP mice to simultaneously delete Vegfr-2 and activate reporter gene expression in endocardial cells. It was found that the b-gal+ descendants of Vegfr-2 null endocardial cells failed to generate intramyocardial coronary arteries in Nfatc1Cre;Vegfr-2f/f;R26fslz embryos (FIG. 6K,L vs. 6M,N). Consistently, coronary angiogenesis assays with ventricles of E11.5 Nfatc1Cre;Vegfr-2f/f;RCEfsEGFP embryos showed that EGFP+ Vegfr-2 null endocardial cells could not respond to Vegf120, they failed to migrate, sprout and form endothelial networks, which was confirmed by quantitative analysis. Thus these results again indicated that the initial coronary arteries arise from the Nfatc1+ precursors in the endocardium and that Vegf signaling is important for this process.

Taken together, the data from the studies of Vegf-a and Vegfr-2 null hearts demonstrate that myocardially produced Vegf-a signals through endocardial Vegfr-2 to stimulate ventricular endocardial cells to undergo angiogenesis that generates coronary arteries. They provide functional evidence that endocardial cells are the progenitors of coronary arteries, whereas the endothelium of coronary veins has a different origin.

Discussion

These studies demonstrated that the endocardium is a major source of endothelial cells of the coronary vasculature. The endocardium generates the precursor cells that form coronary plexuses and develop into endothelial cells of coronary arteries, arterioles and capillaries. Such angiogenic functions of endocardial cells appear evolutionarily conserved, as revealed in transplantation studies in which avian endocardial cells are capable of generating coronary arterial network.

The results show that ventricular endocardial cells are not terminally differentiated but instead are angiogenic for coronary arteries. The angiogenic sprouting and migration of endocardial cells into the myocardium is induced by myocardial Vegf-a to endocardial Vegfr-2 signaling. This is consistent with previous morphological analysis suggesting that the earliest vessels develop when encasing endocardial cells penetrate the myocardium and proliferate into an interconnected coronary network (Viragh and Challice, 1981). In contrast to the requirement for myocardial Vegf-a to endocardial Vegfr2 signaling, neither endocardial deletion of Vegf-a nor proepicardial/epicardial deletion of Vegfr-2 blocked intramyocardial coronary angiogenesis (Zhang et al. unpublished data).

Figure 7A:
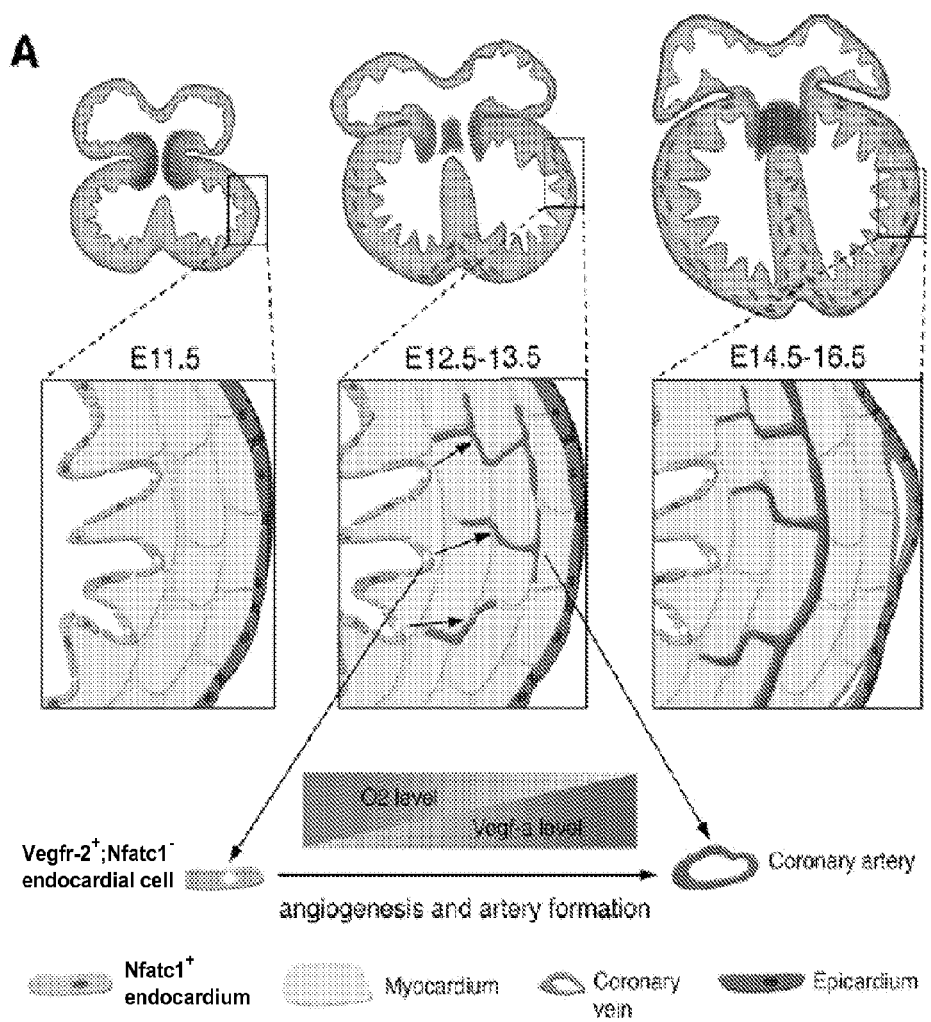
FIG. 7A-7B. Working model of coronary artery formation by endocardial cells (A) Diagram shows an ontogenic role for endocardial cells in generation of the coronary arteries. Between E11.5 and E13.5 of mouse embryogenesis, myocardial proliferation generates a Vegf-a gradient across the thickening ventricular wall, possibly regulated by a reverse gradient of myocardial O2 content. At the same time, some ventricular endocardial cells turn off nuclear Nfatc1 expression (purple nuclei). The Vegf-a gradient induces these Nfatc1− endocardial cells (white nuclei) to invade the myocardium and proliferate into coronary plexuses by angiogenesis via their expression of Vegfr-2. The plexuses then develop into coronary arteries. (B) Knockout of Vegf-a in the myocardium or Vegfr-2 in the endocardium prevents coronary angiogenesis and artery formation, but does not block coronary vein formation, suggesting that coronary veins arise from non-endocardial origins, independent of myocardial Vegf-a to endocardial Vegfr-2 signaling.
Figure 7B:
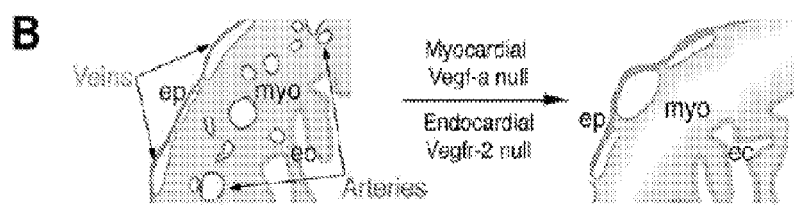

A hypoxia-dependent Vegf-a concentration gradient exists in the myocardium of the developing heart (Wikenheiser et al., 2006), and our results indicate that this gradient provides a cue through Vegfr-2 in the endocardium to trigger migration of angiogenic precursor cells from the endocardium into the myocardium (FIG. 7A). Once in the myocardium, these cells predominantly differentiate into arterial endothelial cells and populate intramyocardial arteries, arterioles, and capillaries.

Analysis showed that Nfatc1 transcription occurs in the endocardium, but not in the descendant endothelial cells of coronary vessels. Thus, while the Nfatc1 promoter is first active in the endocardial cells, it is then shut off as those cells develop into endothelial cells of the coronary plexuses. Previous studies have found that spatiotemporally regulated Nfatc1 expression maintains progenitor cell status and that its down-regulation promotes the differentiation of progenitor cells in the developing heart valves (Wu et al., 2011) or hair follicles (Horsley et al., 2008).

While the endocardium is the source of most arterial endothelial cells, the endocardium provides a lesser contribution to coronary veins. Therefore, the coronary veins have their major origin outside the endocardium and arise by a different mechanism than the arterial cells. Previous fate mapping using an inducible Cre (VE-cadherin-CreERT2) (Monvoisin et al., 2006) showed that the vast majority of the endothelial cells in the coronary veins arise during development by E9.5 from the sinus venosus (Red-Horse et al., 2010). A small number of coronary venous endothelial descendants became coronary artery endothelial cells. While this led to the conclusion that venous endothelial cells are reprogrammed into arterial endothelial cells, the fraction of coronary arterial endothelial cells arising from the sinus venosus was far less than the fraction of coronary venous endothelial cells. Additionally, a recent study using Scx and Sema3D Cre lines suggested that a subset of proepicardial/epicardial cells expressing these genes at E9.5 is able to differentiate into multiple cardiovascular cells, mostly epicardial cells and/or fibroblasts as well as a small fractions of coronary endothelial and smooth muscle cells (Katz et al., 2012). The fate-mapping experiments here also showed that a fraction of the sinus venous endothelial cells are derived from the endocardium, suggesting that endocardial cells may contribute to a minor fraction of the coronary venous endothelium via the sinus venosus route.

Collectively, these results suggest a mechanism for coronary vessel development in which the arterial and venous portions mainly arise from largely distinct embryonic endothelial cell populations at different anatomical sites and during distinct developmental windows. The results showed that around E11.5, endocardial precursor cells, through Vegfr-2, respond to Vegf-a signaling from the myocardium and migrate into the myocardium to form coronary plexuses where they mature into arteries, arterioles, and capillaries. In contrast, the coronary venous endothelial cells arise mostly from sinus venous endothelial cells before E9.5 (Red-Horse et al., 2010).

Materials and Methods

To generate the Nfatc1Cre mice, an IRES-Cre/PGK-hygromycin cassette was inserted at the 3' untranslational region of Nfatc1 (Figure S2). To disrupt Vegf-a in the myocardium, Tnnt2Cre mice (Chen et al., 2006; Jiao et al., 2003) were mated to Vegf-af/fmice (Gerber et al., 1999). Inactivation of Vegfr-2 expression in the endocardium was achieved by crossing Nfatc1Cre with Vegfr-2f/f mice. The maintenance of mice and mouse experiments were performed according to protocols approved by the Institutional Animal Care and Use Committee of Albert Einstein College of Medicine and Vanderbilt University. Noontime on the day of detecting vaginal plugs was designated as E0.5.

Immunostainings and RNA in situ hybridization. For immunostainings, mouse embryos from E9.5 to E12.5 or hearts from E13.5 to E16.5 were fixed in 4% PFA. A 15%-30% sucrose gradient was applied to those for frozen sections Immunohistochemistry was carried out using the ABC-HRP or ABC-AK method (Vector Laboratories). Fluorescent avidin kit (Vector Laboratories) was used for immunofluorescence visualization. Whole mount or section RNA in situ hybridization was performed to detect Nfatc1 or Cre transcripts in E9.5 to E15.5 embryos or hearts using probes for Nfatc1 or Cre mRNA.

Whole mount X-gal Staining Embryos from E9.5 to E12.5 or hearts isolated at E13.5 to E14.5 were fixed in 4% PFA on ice for 30 minutes to 2 hours depending on the developmental stage, washed in PBS, and then stained with freshly prepared X-gal solution for 2 hours at 37° C. or overnight at room temperature. The stained samples were washed by PBS, sectioned, and photographed.

Mouse ventricular explant culture and coronary angiogenesis assay: Ventricles without the atria and sinus venosus were isolated from E10.5 or E11.5 embryos, rinsed with PBS to remove circulating cells and placed in the Matrigel (growth factor reduced, BD Biosciences) in Nunc 4-well plates. The Matrigel was prepared by addition of an equal volume of M199 medium plus 10% FBS with or without a testing growth factor including Vegf120, 164, 189, Vegf-c, Vegf-d, Fgf2 or Fgf9 (R&D Systems). The final concentration of each growth factor was 10 ng/ml. Explants were cultured for 6 days and angiogenesis by the ventricular endocardial cells was photographed.

Dye tracing of ventricular endocardial cells in ventricular explant cultures: E11.5 hearts were microinjected with the Red Fluorescent CMTPX (CellTracker™, Invitrogen) through their ventricles. After a 2-minute incubation on ice, atria and sinuses were removed. Ventricles were then rinsed with PBS and placed in the Matrigel with Vegf120. The transmural migration of the labeled individual endocardial cells and their integration into an endothelial network was photographed.

Quail-to-chick transplantation assays: Quail ventricular endocardium or ventricular apex without the epicardium were isolated from the Hamburger and Hamilton stages (HH) 15/16 quail embryos, labeled with carbon particles for visualization, and implanted at the inner curvature of the atrioventricular junction of HH15/16 chick embryonic hearts. The implanted chick embryos were incubated at 37° C. until HH34 or HH42. The chimerical hearts were isolated and fixed with 3.7% formaldehyde, cut into anterior and posterior halves through the right ventricle to expose intramyocardial vasculature, followed by incubation with a mouse monoclonal anti-QH1 antibody to visualize the contribution of quail endocardial cells to the developing chick coronary vasculature.

REFERENCES

Cai, C. L., Martin, J. C., Sun, Y., Cui, L., Wang, L., Ouyang, K., Yang, L., Bu, L., Liang, X., Zhang, X., et al. (2008). A myocardial lineage derives from Tbx18 epicardial cells. Nature 454, 104-108.

Carmeliet, P., Ferreira, V., Breier, G., Pollefeyt, S., Kieckens, L., Gertsenstein, M., Fahrig, M., Vandenhoeck, A., Harpal, K., Eberhardt, C., et al. (1996). Abnormal blood vessel development and lethality in embryos lacking a single VEGF allele. Nature 380, 435-439.

Chang, C. P., Neilson, J. R., Bayle, J. H., Gestwicki, J. E., Kuo, A., Stankunas, K., Graef, I. A., and Crabtree, G. R. (2004). A field of myocardial-endocardial NFAT signaling underlies heart valve morphogenesis. [see comment]. Cell 118, 649-663.

Chen, J. W., Zhou, B., Yu, Q. C., Shin, S. J., Jiao, K., Schneider, M. D., Baldwin, H. S., and Bergelson, J. M. (2006). Cardiomyocyte-specific deletion of the coxsackievirus and adenovirus receptor results in hyperplasia of the embryonic left ventricle and abnormalities of sinuatrial valves. Circ Res 98, 923-930.

de la Pompa, J. L., Timmerman, L. A., Takimoto, H., Yoshida, H., Elia, A. J., Samper, E., Potter, J., Wakeham, A., Marengere, L., Langille, B. L., et al. (1998). Role of the NF-ATc transcription factor in morphogenesis of cardiac valves and septum. [see comment]. Nature 392, 182-186.

Dettman, R. W., Denetclaw, W., Jr., Ordahl, C. P., and Bristow, J. (1998). Common epicardial origin of coronary vascular smooth muscle, perivascular fibroblasts, and intermyocardial fibroblasts in the avian heart. Dev Biol 193, 169-181.

Drake, C. J., and Fleming, P. A. (2000). Vasculogenesis in the day 6.5 to 9.5 mouse embryo. Blood 95, 1671-1679.

Ferrara, N., Carver-Moore, K., Chen, H., Dowd, M., Lu, L., O'Shea, K. S., Powell-Braxton, L., Hillan, K. J., and Moore, M. W. (1996). Heterozygous embryonic lethality induced by targeted inactivation of the VEGF gene. Nature 380, 439-442.

Gerber, H. P., Hillan, K. J., Ryan, A. M., Kowalski, J., Keller, G. A., Rangell, L., Wright, B. D., Radtke, F., Aguet, M., and Ferrara, N. (1999). VEGF is required for growth and survival in neonatal mice. Development 126, 1149-1159.

Giordano, F. J., Gerber, H. P., Williams, S. P., VanBruggen, N., Bunting, S., Ruiz-Lozano, P., Gu, Y., Nath, A. K., Huang, Y., Hickey, R., et al. (2001). A cardiac myocyte vascular endothelial growth factor paracrine pathway is required to maintain cardiac function. Proc Natl Acad Sci USA 98, 5780-5785.

Gustafsson, E., Brakebusch, C., Hietanen, K., and Fassler, R. (2001). Tie-1-directed expression of Cre recombinase in endothelial cells of embryoid bodies and transgenic mice. J Cell Sci 114, 671-676.

Haigh, J. J., Morelli, P. I., Gerhardt, H., Haigh, K., Tsien, J., Damert, A., Miquerol, L., Muhlner, U., Klein, R., Ferrara, N., et al. (2003). Cortical and retinal defects caused by dosage-dependent reductions in VEGF-A paracrine signaling. Dev Biol 262, 225-241.

Horsley, V., Aliprantis, A. O., Polak, L., Glimcher, L. H., and Fuchs, E. (2008). NFATc1 balances quiescence and proliferation of skin stem cells. Cell 132, 299-310.

Jiao, K., Kulessa, H., Tompkins, K., Zhou, Y., Batts, L., Baldwin, H. S., and Hogan, B. L. (2003). An essential role of Bmp4 in the atrioventricular septation of the mouse heart. Genes Dev 17, 2362-2367.

Katz, T. C., Singh, M. K., Degenhardt, K., Rivera-Feliciano, J., Johnson, R. L., Epstein, J. A., and Tabin, C. J. (2012). Distinct compartments of the proepicardial organ give rise to coronary vascular endothelial cells. Developmental cell 22, 639-650.

Komiyama, M., Ito, K., and Shimada, Y. (1987). Origin and development of the epicardium in the mouse embryo. Anat Embryol (Berl) 176, 183-189.

Kraus, F., Haenig, B., and Kispert, A. (2001). Cloning and expression analysis of the mouse T-box gene Tbx18. Mech Dev 100, 83-86.

Lavine, K. J., and Ornitz, D. M. (2009). Shared circuitry: developmental signaling cascades regulate both embryonic and adult coronary vasculature. Circ Res 104, 159-169.

Luttun, A., and Carmeliet, P. (2003). De novo vasculogenesis in the heart. Cardiovascular Research 58, 378-389.

Majesky, M. W. (2004). Development of coronary vessels. Curr Top Dev Biol 62, 225-259.

Mikawa, T., Borisov, A., Brown, A. M., and Fischman, D. A. (1992). Clonal analysis of cardiac morphogenesis in the chicken embryo using a replication-defective retrovirus: I. Formation of the ventricular myocardium. Dev Dyn 193, 11-23.

Mikawa, T., and Fischman, D. A. (1992). Retroviral analysis of cardiac morphogenesis: discontinuous formation of coronary vessels. Proc Natl Acad Sci USA 89, 9504-9508.

Mikawa, T., and Gourdie, R. G. (1996). Pericardial mesoderm generates a population of coronary smooth muscle cells migrating into the heart along with ingrowth of the epicardial organ. Dev Biol 174, 221-232.

Miquerol, L., Langille, B. L., and Nagy, A. (2000). Embryonic development is disrupted by modest increases in vascular endothelial growth factor gene expression. Development 127, 3941-3946.

Misfeldt, A. M., Boyle, S. C., Tompkins, K. L., Bautch, V. L., Labosky, P. A., and Baldwin, H. S. (2009). Endocardial cells are a distinct endothelial lineage derived from Flk1+ multipotent cardiovascular progenitors. Dev Biol 333, 78-89.

Miyoshi, G., Hjerling-Leffler, J., Karayannis, T., Sousa, V. H., Butt, S. J., Battiste, J., Johnson, J. E., Machold, R. P., and Fishell, G. (2010). Genetic fate mapping reveals that the caudal ganglionic eminence produces a large and diverse population of superficial cortical interneurons. The Journal of neuroscience: the official journal of the Society for Neuroscience 30, 1582-1594.

Monvoisin, A., Alva, J. A., Hofmann, J. J., Zovein, A. C., Lane, T. F., and Iruela-Arispe, M. L. (2006). VE-cadherin-CreERT2 transgenic mouse: a model for inducible recombination in the endothelium. Dev Dyn 235, 3413-3422.

Olivey, H. E., and Svensson, E. C. Epicardial-myocardial signaling directing coronary vasculogenesis. Circ Res 106, 818-832.

Olivey, H. E., and Svensson, E. C. (2010). Epicardial-myocardial signaling directing coronary vasculogenesis. Circulation Research 106, 818-832.

Perez-Pomares, J. M., Carmona, R., Gonzalez-Iriarte, M., Atencia, G., Wessels, A., and Munoz-Chapuli, R. (2002). Origin of coronary endothelial cells from epicardial mesothelium in avian embryos. Int J Dev Biol 46, 1005-1013.

Ranger, A. M., Grusby, M. J., Hodge, M. R., Gravallese, E. M., de la Brousse, F. C., Hoey, T., Mickanin, C., Baldwin, H. S., and Glimcher, L. H. (1998). The transcription factor NFATc is essential for cardiac valve formation. [see comment]. Nature 392, 186-190.

Red-Horse, K., Ueno, H., Weissman, I. L., and Krasnow, M. A. (2010). Coronary arteries form by developmental reprogramming of venous cells. Nature 464, 549-553.

Shalaby, F., Rossant, J., Yamaguchi, T. P., Gertsenstein, M., Wu, X. F., Breitman, M. L., and Schuh, A. C. (1995). Failure of blood-island formation and vasculogenesis in Flk-1-deficient mice. Nature 376, 62-66.

Soriano, P. (1999). Generalized lacZ expression with the ROSA26 Cre reporter strain. Nature Genetics 21, 70-71.

Sousa, V. H., Miyoshi, G., Hjerling-Leffler, J., Karayannis, T., and Fishell, G. (2009). Characterization of Nkx6-2-derived neocortical interneuron lineages. Cerebral cortex 19 Suppl 1, i1-10.

Sugi, Y., and Markwald, R. R. (1996). Formation and early morphogenesis of endocardial endothelial precursor cells and the role of endoderm. Developmental Biology 175, 66-83.

Tomanek, R. J., Ishii, Y., Holifield, J. S., Sjogren, C. L., Hansen, H. K., and Mikawa, T. (2006). VEGF family members regulate myocardial tubulogenesis and coronary artery formation in the embryo. Circ Res 98, 947-953.

Viragh, S., and Challice, C. E. (1981). The origin of the epicardium and the embryonic myocardial circulation in the mouse. Anat Rec 201, 157-168.

Vrancken Peeters, M. P., Gittenberger-de Groot, A. C., Mentink, M. M., and Poelmann, R. E. (1999). Smooth muscle cells and fibroblasts of the coronary arteries derive from epithelial-mesenchymal transformation of the epicardium. Anat Embryol (Berl) 199, 367-378.

Wada, A. M., Willet, S. G., and Bader, D. (2003). Coronary vessel development: a unique form of vasculogenesis. Arterioscler Thromb Vasc Biol 23, 2138-2145.

Wikenheiser, J., Doughman, Y. Q., Fisher, S. A., and Watanabe, M. (2006). Differential levels of tissue hypoxia in the developing chicken heart. Dev Dyn 235, 115-123.

Wu, B., Wang, Y., Lui, W., Langworthy, M., Tompkins, K. L., Hatzopoulos, A. K., Baldwin, H. S., and Zhou, B. (2011). Nfatc1 coordinates valve endocardial cell lineage development required for heart valve formation. Circulation Research 109, 183-192.

Yamashita, J., Itoh, H., Hirashima, M., Ogawa, M., Nishikawa, S., Yurugi, T., Naito, M., and Nakao, K. (2000). Flk1-positive cells derived from embryonic stem cells serve as vascular progenitors. [see comment]. Nature 408, 92-96.

Yang, L., Soonpaa, M. H., Adler, E. D., Roepke, T. K., Kaltman, S. J., Kennedy, M., Henckaerts, E., Bonham, K., Abbott, G. W., Linden, R. M., et al. (2008). Human cardiovascular progenitor cells develop from a KDR+ embryonic-stem-cell-derived population. Nature 453, 524-528.

Zhou, B., Cron, R. Q., Wu, B., Genin, A., Wang, Z., Liu, S., Robson, P., and Baldwin, H. S. (2002). Regulation of the murine Nfatc1 gene by NFATc2. Journal of Biological Chemistry 277, 10704-10711.

Zhou, B., Ma, Q., Rajagopal, S., Wu, S. M., Domian, I., Rivera-Feliciano, J., Jiang, D., von Gise, A., Ikeda, S., Chien, K. R., et al. (2008). Epicardial progenitors contribute to the cardiomyocyte lineage in the developing heart. Nature 454, 109-113.

Zhou, B., Wu, B., Tompkins, K. L., Boyer, K. L., Grindley, J. C., and Baldwin, H. S. (2005). Characterization of Nfatc1 regulation identifies an enhancer required for gene expression that is specific to pro-valve endocardial cells in the developing heart. Development 132, 1137-1146.

What is claimed is:

1. A method for producing an artery-specific endothelial cell comprising contacting an Nfatc1+ endocardial cell with an amount of an agent that activates Vegfr-2 effective to produce an artery-specific endothelial cell from the Nfatc1+ endocardial cell.

2. The method of claim 1, wherein the artery-specific endothelial cell is a coronary artery-specific endothelial cell.

3. The method of claim 1, wherein the Nfatc1+ endocardial cell is contacted with the agent that activates Vegfr-2.

4. The method of claim 1, wherein the Nfatc1+ endocardial cell is contacted with an agent that activates human Vegfr-2.

5. The method of claim 1, wherein the agent that activates Vegfr-2 is Vegf-a.

6. The method of claim 5, wherein the Vegf-a is human Vegf-a.

7. The method of claim 1, wherein the endocardial cell is obtained from a ventricular endocardium.

8. A composition comprising a plurality of isolated artery-specific endothelial cells produced by the method of claim 1.

9. The composition of claim 8, wherein the composition is 90% or greater isolated artery-specific endothelial cells.

10. The composition of claim 9, wherein the composition is 99% or greater isolated artery-specific endothelial cells.

11. A method of treating a heart condition in a mammalian subject comprising administering to the subject an amount of the artery-specific endothelial cells produced by claim 1 effective to treat the heart condition in a mammalian subject.

12. The method of claim 11, wherein a symptom of the heart condition is a diseased coronary artery of the heart.

13. The method of claim 11, wherein the heart condition is atherosclerosis or heart infarction.

14. A method of determining whether an agent specifically promotes the growth of coronary artery-specific endothelial cells comprising contacting an Nfatc1+ endocardial cell with an amount of an activator of Vegfr-2 or of Vegf-a under conditions permitting the cell to produce an artery-specific endothelial cell from the Nfatc1+ endocardial cell, and measuring the extent of growth of the artery-specific endothelial cell in the presence of, and in the absence of, the agent, wherein an increased growth of artery-specific endothelial cells in the presence of the agent as compared to in the absence of the agent indicates that the agent specifically promotes the growth of coronary artery-specific endothelial cells, and wherein a decreased, or no increase in, growth of artery-specific endothelial cells in the presence of the agent as compared to in the absence of the agent indicates that the agent does not specifically promote the growth of coronary artery-specific endothelial cells.

15. The method of claim 14, wherein the agent is a small organic molecule, a peptide, an RNAi agent, a nucleic acid, an antibody or an antibody fragment.

* * * * *